United States Patent [19]

Hubbard et al.

[11] 4,372,301
[45] Feb. 8, 1983

[54] ARM SLING

[75] Inventors: Vance M. Hubbard, Euless; Welton K. Brunson, Bedford, both of Tex.

[73] Assignee: Tecnol, Inc., Fort Worth, Tex.

[21] Appl. No.: 254,192

[22] Filed: Apr. 14, 1981

[51] Int. Cl.³ .............................................. A61F 5/40
[52] U.S. Cl. .................................. 128/94; 24/265 R
[58] Field of Search ............................ 128/94, 83, 82; 24/265 R, 265 A, 265 EC, 265 AL, 248 R, 132 AA, 132 WL, 115 A, 129 B

[56] References Cited

U.S. PATENT DOCUMENTS

| | | | |
|---|---|---|---|
| 2,594,809 | 4/1952 | Sanders | 128/94 |
| 3,686,711 | 8/1972 | Kuramoto et al. | 24/265 R |

OTHER PUBLICATIONS

Shoulder Immobilizer and Velpeau Dressing, Zimmer Catalogue, Jan. 1974, p. 54.

Primary Examiner—John D. Yasko
Attorney, Agent, or Firm—Jerry W. Mills

[57] ABSTRACT

A universal arm sling and shoulder immobilizer (10) is provided. The shoulder immobilizer (10) includes a sling trough (14) having first and second ends (26, 28) with the first end (26) closed for allowing the elbow of the arm to abut the closed end (26). The sling trough (14) is constructed of flexible material allowing the second end (28) to be folded towards the first end (26) for shortening the length of the sling trough (14) for providing a sling of a desired length thus allowing the shoulder immobilizer (10) to accommodate a wide range of limb sizes. A support strap (16) of variable length is provided and is secured to the first end of the sling trough (14) and is of sufficient length to extend across the back of the wearer, over the opposite shoulder and to the top portion of the sling trough (14) adjacent the second end (28) thereof. A restraining strap (18) is provided for securing the limb supported by the sling trough (14) adjacent the chest of the wearer thus providing shoulder immobilization.

11 Claims, 15 Drawing Figures

ARM SLING

TECHNICAL FIELD

This invention relates to medical devices and more particularly to arm slings and shoulder immobilizers.

BACKGROUND ART

Because humans have limbs and trunks of different sizes, it is necessary to have arm slings and shoulder immobilizers of various sizes to achieve a proper fit. Therefore, most hospitals and other outlets for dispensing arm slings and shoulder immobilizers stock arm slings and shoulder immobilizers varying in size from extra-small to extra-large. Further, every one of these sizes requires separate inventoring and ordering.

Thus, a need exists for an arm sling and shoulder immobilizer of universal size which allows adjustment to fit each patient's individual needs. Finally, it would be desirable to have a sling and shoulder immobilizer that could be rapidly adjusted and provide a custom fit on a patient.

DISCLOSURE OF THE INVENTION

In accordance with the present invention, a universal arm sling is provided that is capable of being adjusted to fit patients within a wide size range. A shoulder immobilizer having similar characteristics is also provided. The sling consists of a sling trough of variable length, support strap, and fastener. The shoulder immobilizer also incorporates a restraining strap and additional fasteners. The fasteners allow for rapidly and effectively securing the sling trough, support strap and shoulder restraining strap to the patient to achieve a desired fit.

More particularly, an arm sling for a person is provided that includes a sling trough of a predetermined unfolded length, having first and second ends, for supporting a forearm, with the first end being closed for allowing the elbow of the arm to abut that end. The sling trough is constructed of flexible material allowing the second end to be folded towards the first end for shortening the length of the sling trough for providing a sling of a desired length, so that forearms of various sizes can be accommodated. In this manner, the sling trough can be adjusted to fit the arm length of the patient. A support strap is secured to the first end of a sling trough and is of sufficient length to traverse the back, extend over the shoulder opposite the arm which is in the sling and extend to the top portion of the sling trough adjacent the second end thereof. Structure is provided for securing the support strap adjacent the second end of the sling trough, regardless of the folded length, for supporting the arm in the desired position in the sling.

In accordance with another aspect of the present invention, a fastener is provided for securing the support strap of the sling adjacent the second end of the sling therethrough and a second member hinged to the first member. The second member has an aperture for allowing the strap to be passed therethrough. The first and second members of the fastener can be secured in superimposed relationship and attached to the sling trough. The support strap for the sling is looped through the apertures in the fastener and is adjustable for length.

In accordance with another aspect of the present invention, a universal shoulder immobilizer is provided. The shoulder immobilizer utilizes the same components as the universal arm sling of the present invention and further includes a restraining strap of adjustable length for encircling the back of a person wearing the immobilizer. The restraining strap is secured to the first end or elbow end of the sling trough and is of sufficient length to extend from that end of the sling trough around the back of the person to the second end of the sling trough, where the restraining strap is also secured. Thus, the restraining strap and the sling trough encircle the torso of a person and by adjusting the length of the restraining strap the desired amount of shoulder immobilization is achieved.

Both the support and restraining straps preferably utilize hook and loop fasteners for allowing the length of the straps to be adjusted as desired. Thus, the unique combination of the support strap, fastener and sling trough of variable length results in a universal sling that can be custom fitted on each patient while allowing quick and easy application of the sling upon the arm. Thus, in accordance with the present invention, an exact size sling and shoulder immobilizer is provided.

DESCRIPTION OF THE DRAWINGS

The present invention and its advantages can be more completely understood by reference to the accompanying drawings taken in conjunction with the Detailed Description in which.

DETAILED DESCRIPTION

Figure 1:
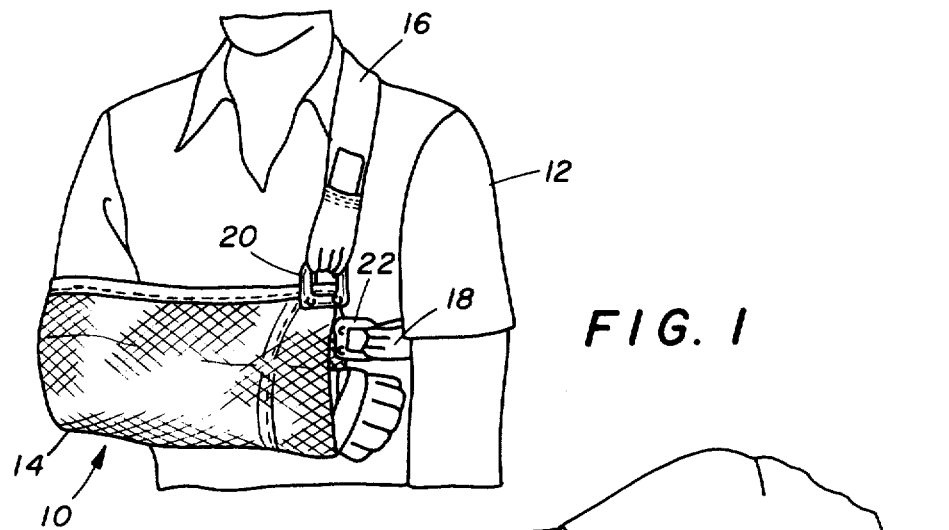
FIG. 1 illustrates the shoulder immobilizer of the present invention being worn by a patient.
Figure 2:
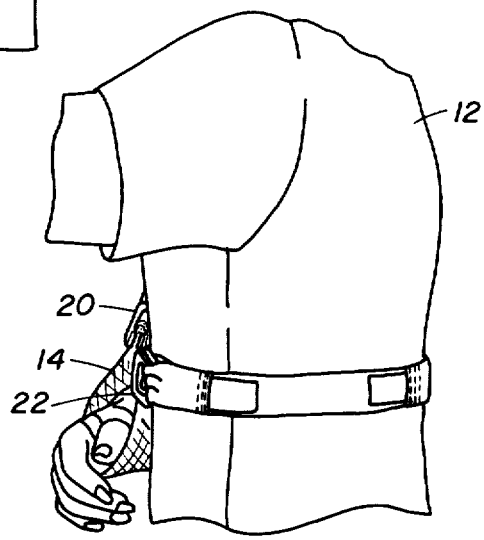
FIG. 2 is an illustration of the left side of the patient shown in FIG. 1 and illustrates a portion of the shoulder immobilizer worn by that patient.
Figure 3:
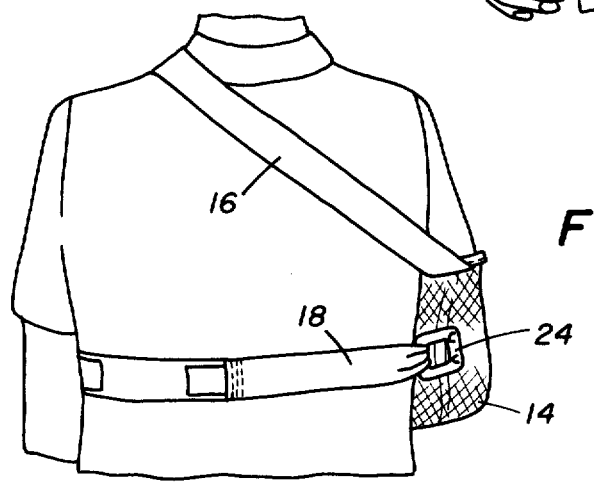
FIG. 3 is an illustration of the back of the patient of FIG. 1 and a portion of the shoulder immobilizer worn by that patient.

Referring to the drawings, where like reference numerals indicate like elements throughout, there is illustrated a universal shoulder immobilizer in accordance with the invention, generally referred to by reference numeral 10. As shown in FIG. 1, shoulder immobilizer 10 is being worn by a human patient 12. FIGS. 2 and 3 illustrate other views of patient 12 wearing shoulder immobilizer 10.

Shoulder immobilizer 10 includes several components including a sling trough 14, a support strap 16, a restraining strap 18 and snap locking fasteners 20, 22 and 24.

As illustrated in FIGS. 1-3, the right arm and shoulder of patient 12 is being immobilized by shoulder immobilizer 10. Support strap 16 is not shown in FIG. 3. It is to be understood that the universal sling in accordance with the present invention utilizes the same components as shoulder immobilizer 10 except that the sling does not include restraining strap 18 and snap locking fasteners 22 and 24. Thus, shoulder immobilizer 10 utilizes restraining strap 18 and snap locking fasteners 22 and 24 to transform the universal sling of the invention into universal shoulder immobilizer 10.

Figure 4:
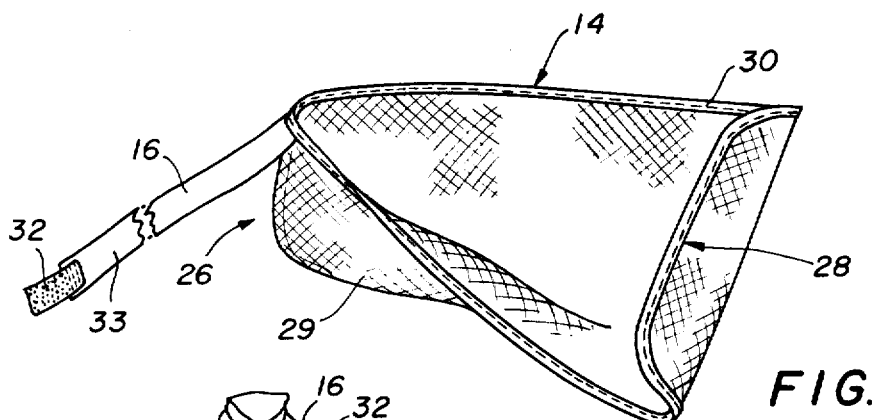
FIG. 4 is a perspective view of a sling trough and support strap in accordance with the present invention.

FIG. 4 illustrates sling trough 14 and a portion of supporting strap 16. Sling trough 14 is generally U-shaped and has a first end or elbow end 26 which is closed and a second end or open end 28. Preferably, the length of sling trough in an unfolded position is of a length sufficient to accommodate a very long forearm. Sling trough 14 is constructed of a flexible material that allows second end 28 to be folded toward first end 26 to adjust sling trough 14 to the desired length to fit a particular forearm length. The material of sling trough 14 is preferably a polyester or nylon mesh. Use of a mesh material for sling trough 14, or a material having a plurality of holes along the length of sling trough 14 is preferred because this allows snap locking fasteners, such as 20, to be attached to sling trough 14 at a desired location, which helps to provide an exact custom fit. Further, such material flows air circulation through the material thereby providing additional comfort for the wearer. Preferably, when a mesh type material is used, a binding 30 is sewn or otherwise attached along the border of material 29 which is utilized for sling trough 14. Binding 30 helps prevent material 29 from unraveling. As shown in FIG. 4, one end of support strap 16 is attached to first end 26 of sling trough 14. This attachment may be made by any suitable method such as by sewing support strap 16 to binding 30 or material 29. Also, a snap locking fastener, such as snap locking fastener 20, could also be utilized to fasten that end of support strap 16 to end 26 of sling trough 14.

FIG. 4 also illustrates the end portion 32 of support strap 16 that is opposite the end 33 which is attached to first end 26 of sling trough 14. End 32 of support strap 16 is preferably part of a hook and loop or other similar type fastener, such as those available under the name Velcro. End 32 of support strap 16 is preferably the hook portion of the fastener, having a plurality of hook projections and the loop portion 34 of the fastener is located along at least part of the length of supporting strap 16. Both hook portion and loop portion 34 of the fastener are located on the same side of supporting strap 16. This allows the hook portion at end 32 to be folded over and mate with loop portion 34 to form a loop, for allowing support strap 16 to be secured to snap locking fastener 20. The construction of restraining strap 18 is similar to that of support strap 16, except that in the embodiment shown, each end of the restraining strap 18 terminates with a hook and loop fastener. It is to be understood that support strap 16 could also be constructed in this manner.

Figure 12:
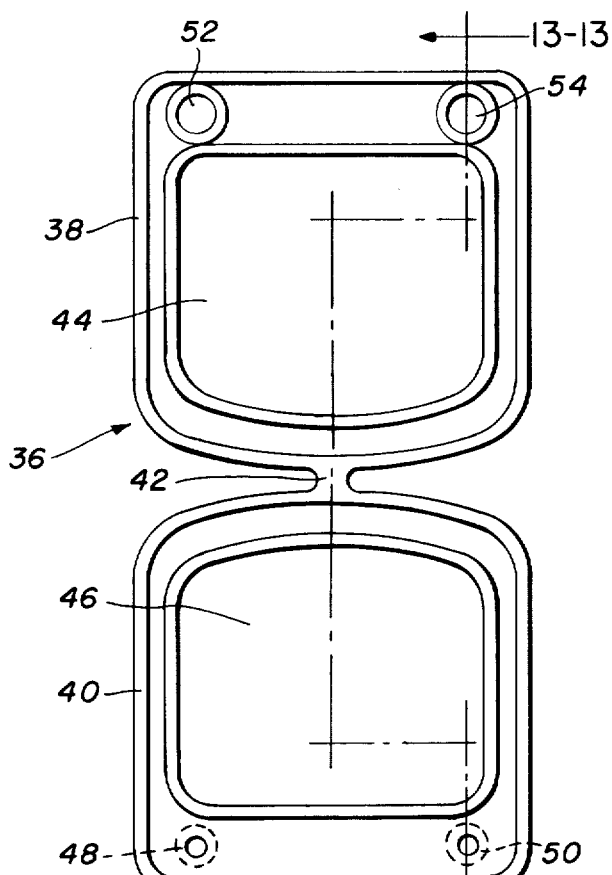
FIG. 12 is an elevational view of a fastener in accordance with the invention.
Figure 13:
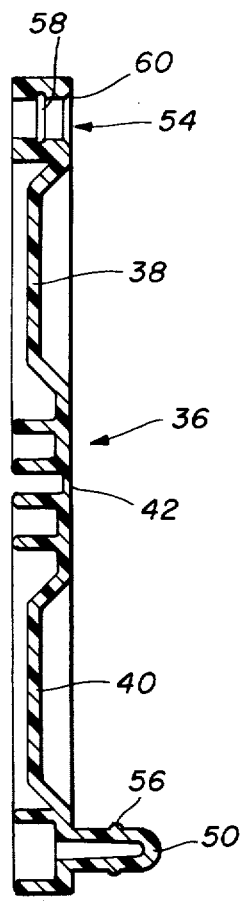
FIG. 13 is a sectional view along lines 13—13 of FIG. 12.

Referring to FIGS. 12-15, there is illustrated a snap locking fastener 36 in accordance with the present invention. Snap locking fastener 36 is similar to snap locking fasteners 20, 22 and 24. As illustrated, snap locking fastener 36 includes a first member 38 and a second member 40. As illustrated in FIGS. 12 and 13, first and second members 38 and 40 are generally planar and are hinged together by a hinge 42. Hinge 42 may comprise, for example, a flexible polymeric material, but the use of this type of hinge is not a limitation on the present invention as any suitable hinge can be utilized.

Figure 14:
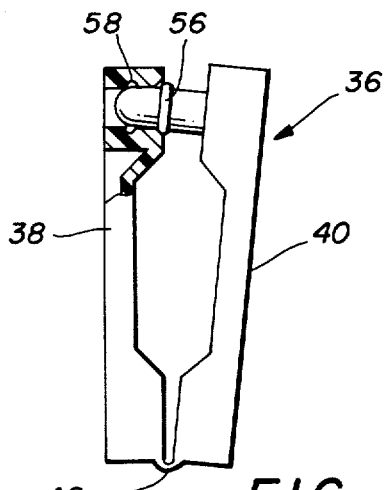
FIG. 14 is a side view, partly in section, of the fastener shown in FIG. 12 in a partially closed position.
Figure 15:
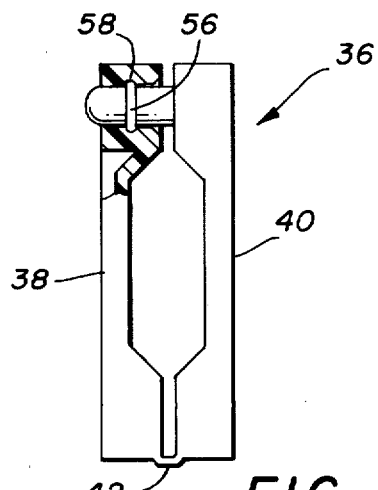
FIG. 15 is a side elevational view, partly in section, of the fastener shown in FIG. 12 in a fully closed position.

Each of members 38 and 40 of snap locking fastener 36 include an aperture 44 and 46, respectively, of sufficient size to allow either support strap 16 or restraining strap 18 to be passed therethrough. Snap locking fastener 36 includes a provision for securing first member 38 and second member 40 in a superimposed relationship as shown in FIG. 15. Snap locking fastener 36 includes first pin member 48 and second pin member 50 located on second member 40. Holes 52 and 54 are located in first member 38 and are complimentary to first pin member 48 and second pin member 50, respectively. Preferably, pin members 48 and 50 each have a radially enlarged portion 56 and each of holes 52 and 54 have a correspondingly radially enlarged portion 58. Preferably, each of holes 52 and 54 are beveled slightly at the area indicated by reference numeral 60 in FIG. 13. The foregoing described arrangement allows snap locking fastener 36 to be partially closed as illustrated in FIG. 14 wherein a portion of pin members 48 and 50 are inserted into holes 52 and 54, respectively and radially enlarged portion 56 abuts bevel 60 of hole 52. In the fully closed position, illustrated in FIG. 15, first member 38 and second member 40 are facing each other or superimposed. Each of pin members 48 and 50 are mated in a force fit relationship with holes 52 and 54, respectively. Radially enlarged portion 56 of the pin members which are mated with radially enlarged portion 58 of holes 52 and 54 which further restrain members 38 and 40 from being separated. Preferably, snap locking fastener 36 is constructed from a plastic or suitable polymeric material, such as polystyrene, for example.

Figure 5:
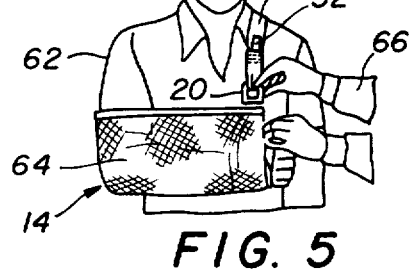
FIGS. 5-11 illustrate the shoulder immobilizer of the present invention being applied to and adjusted on a patient.

Referring to FIGS. 5-11, there is illustrated a patient 62 being outfitted with shoulder immobilizer 10 in various stages of adjustment. In FIG. 5, sling trough 14 of shoulder immobilizer 10 has been folded to achieve the desired length and the right forearm 64 of patient 62 has been placed therein. Support strap 16 which is attached to elbow end 26 of sling trough 14 and placed around the back and over the left shoulder of patient 62 by a helper 66. End 32 of support strap 16 has been placed through apertures 44 and 46 of snap locking fastener 20 and has been attached to a loop portion of the hook and loop fastener such that the desired length for support strap 16 has been obtained.

Figure 6:
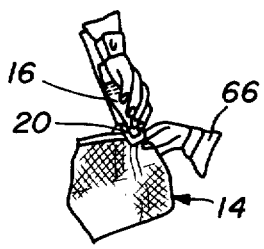
Figure 7:
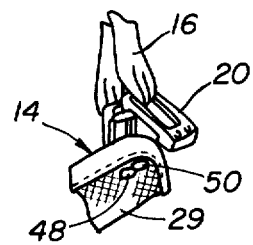
Figure 8:
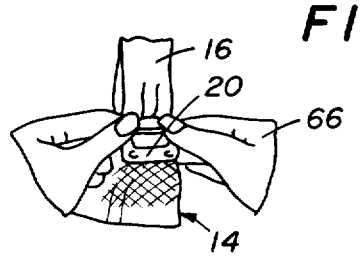

In FIGS. 6-8 there is illustrated the pin members 48 and 50 of snap locking fastener 20 being inserted through the mesh openings of sling trough 14 adjacent second end or open end 28 of sling trough 14. Thus pin members 48 and 50 are preferably of smaller diameter than the diameter of the openings in the mesh fabric of sling trough 14. Preferably, pin members 48 and 50 extend through both sides of sling trough 14, thereby closing the top portion of U-shaped sling trough 14 adjacent second end 28.

In FIG. 8 helper 66 is snap locking fastener 20 by applying sufficient pressure such that pin members 48 and 50 are engaged in a force fit relationship as previously described.

Figure 9:
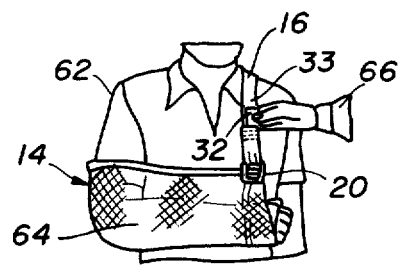

In FIG. 9, a final adjustment of the length of support strap 16 is being made by helper 66 mating hook portion 32 with loop portion 33 in the desired position such that the proper support position for forearm 64 is achieved.

Figure 10:
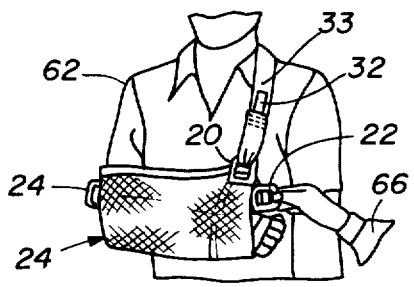
Figure 11:
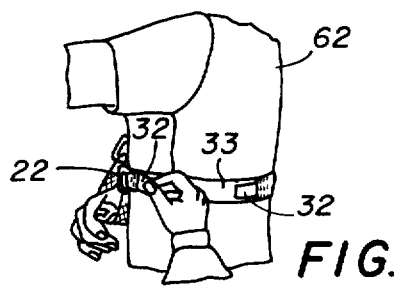

FIGS. 10 and 11 illustrate the attachment of restraining strap 18 utilizing snap locking fasteners 22 and 24. Snap locking fastener 24 is attached to end 26 of sling trough 14 in a manner similar to that described with respect to snap locking fastener 20. One end of restraining strap 18 is looped through snap locking fastener 24 and secured to the surface of restraining strap 18 as shown in FIG. 11. The other end of restraining strap 18 is looped through snap locking fastener 22, shown in FIGS. 10 and 11, and snap locking member 22 is fastened to end 28 of sling trough 14 in a manner similar to that described for snap locking member 20. The length of restraining strap 18 is then adjusted as desired by securing the end portion of restraining strap 18 which is hook portion 32 to the desired location on loop portion 33 as shown in FIG. 11.

Thus, the present invention provides a universal arm sling and shoulder immobilizer allowing a quick and easy application of the apparatus on the arm. The universal size and easy application to a patient reduces the amount of time necessary for medical personnel to attach the sling or shoulder immobilizer to a patient. Further, a custom fit is achieved from the universal arm sling or shoulder immobilizer of the present invention while eliminating the need to maintain arm slings and shoulder immobilizers of different sizes.

While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

We claim:

1. An arm sling for a person comprising a sling trough of a predetermined unfolded length for supporting a forearm, said sling trough having first and second ends, said first end closed for allowing the elbow of the arm to abut the closed end, said trough being constructed of flexible material for allowing the second end to be folded towards the first end for shortening the length of said sling trough for providing a sling of a desired length;

a support strap secured to said first end, said support strap of sufficient length for traversing the back and the shoulder opposite the arm which is in the sling and extend to the top portion of said sling trough adjacent the second end of said sling trough;

fastener means for securing said support strap to said sling trough adjacent the second end of said sling trough including a first member having a first aperture therein for allowing said support strap to be passed therethrough, a second member hinged to said first member, said second member having a first aperture for allowing said support strap to be passed therethrough and;

means for securing said first and second members in superimposed relationship including at least one pin means extending from said first member, said second member having a hole complimentary with said pin means, said pin means engagable in a mating force fit relationship with said hole when said first and second members are superimposed and said pin means is inserted in said hole.

2. The arm sling as recited in claim 1, wherein said flexible material is an open mesh fabric.

3. The arm sling as recited in claim 1 wherein said pin means comprises a cylindrical pin having a radially enlarged portion intermediate the ends of said pin and wherein said complimentary hole includes a radially extending groove complimentary with said radially enlarged portion.

4. The arm sling as recited in claims 1 or 2 wherein said fastener is attached to said sling trough by said means for securing said first and second members.

5. The arm sling as recited in claim 1 wherein said support strap includes means for adjusting the length of said support strap.

6. The arm sling as recited in claim 5 wherein said means for adjusting the length of said strap includes a plurality of hook members located at the end of said strap and a loop portion located along at least part of the length of said support strap to which said hook members can be attached.

7. The arm sling as recited in claim 1 further comprising means for retaining the arm supported by the sling against the chest of the person wearing the sling for immobilizing the shoulder to which the arm in the sling is attached.

8. The arm sling as recited in claim 7 wherein said means for retaining the arm against the chest includes a restraining strap means having two ends, one end secured to said first end of said sling trough, said strap for encircling the back of the person wearing the sling and securable to the second end of said sling trough for restraining movement of the arm carried by the sling thereby preventing movement of the shoulder to which the arm is attached.

9. The arm sling as recited in claim 8 wherein said restraining strap is of variable length.

10. The fastener comprising a first member having a first aperture therein, a second member hinged to said first member, said second member having a first aperture and means for securing said first and second members in superimposed relationship such that said apertures are aligned to provide a passageway through said fastener when said first and second members are superimposed, said securing means including at least one pin means extending from said first member, said second member having a complimentary hole for each of said pin means, each of said pin means engagable in mating force fit relationship with a different one of said holes when said first and second members are superimposed.

11. The fastener as recited in claim 10 wherein said pin means comprises a cylindrical pin having a radially enlarged portion intermediate the ends of said pin and wherein said complimentary hole includes a radially extending groove complimentary with said radially enlarged portion.

* * * * *